(12) United States Patent
Lopez Camacho et al.

(10) Patent No.: US 11,986,223 B2
(45) Date of Patent: May 21, 2024

(54) ADJUSTABLE IMPLANT WITH ADVANCED SEALING AND RETENTION

(71) Applicant: Nuvasive Specialized Orthopedics, Inc., San Diego, CA (US)

(72) Inventors: Jorge Lopez Camacho, Oxnard, CA (US); Woong Kim, Fresno, CA (US); Shawn Placie, Aliso Viejo, CA (US)

(73) Assignee: NuVasive Specialized Orthopedics, Inc., San Diego, CA (US)

( * ) Notice: Subject to any disclaimer, the term of this patent is extended or adjusted under 35 U.S.C. 154(b) by 0 days.

(21) Appl. No.: 18/008,830

(22) PCT Filed: Jun. 1, 2022

(86) PCT No.: PCT/US2022/031709
§ 371 (c)(1),
(2) Date: Dec. 7, 2022

(87) PCT Pub. No.: WO2022/256367
PCT Pub. Date: Dec. 8, 2022

(65) Prior Publication Data
US 2023/0190341 A1 Jun. 22, 2023

Related U.S. Application Data

(60) Provisional application No. 63/209,987, filed on Jun. 12, 2021, provisional application No. 63/197,192, filed on Jun. 4, 2021.

(51) Int. Cl.
*A61B 17/72* (2006.01)
*A61B 17/68* (2006.01)

(52) U.S. Cl.
CPC .... *A61B 17/7225* (2013.01); *A61B 2017/681* (2013.01); *A61B 17/7216* (2013.01)

(58) Field of Classification Search
CPC ............ A61B 17/7216; A61B 17/7225; A61B 17/7013; A61B 17/7014; A61B 17/7016;
(Continued)

(56) References Cited

U.S. PATENT DOCUMENTS 3,976,060 A * 8/1976 Hildebrandt ....... A61B 17/8004
606/241
7,753,915 B1 * 7/2010 Eksler ................ A61B 17/7016
606/86 R
(Continued)

FOREIGN PATENT DOCUMENTS

| FR | 2726460 A1 * | 5/1996 | ......... A61B 17/7216 |
| FR | 2726460 A1 | 5/1996 | |
| WO | 2020/135088 A1 | 7/2020 | |

OTHER PUBLICATIONS

International Search Report and Written Opinion, International Application No. PCT/US2022/031709, dated Nov. 18, 2022, 17 pages.

*Primary Examiner* — Lynnsy M Summitt

(57) ABSTRACT

Various implementations include an adjustable implant such as a distraction/compression device. In certain cases, the adjustable implant can include a housing; an adjustable member at least partially positioned within the housing and configured to translate relative to the housing; and an intermediary member positioned between the housing and the adjustable member.

17 Claims, 7 Drawing Sheets

(58) Field of Classification Search
CPC ............ A61B 17/7017; A61B 17/7019; A61B 17/7052; A61B 17/8004; A61B 17/8023
See application file for complete search history.

(56) References Cited

U.S. PATENT DOCUMENTS

| | | | | |
|---|---|---|---|---|
| 8,449,543 | B2 * | 5/2013 | Pool | A61B 17/7216 606/62 |
| 10,918,425 | B2 * | 2/2021 | Schwardt | A61B 17/62 |
| 2019/0328425 | A1 * | 10/2019 | Sharifi-Mehr | A61B 17/663 |
| 2022/0346846 | A1 * | 11/2022 | Pool | A61B 17/8888 |

* cited by examiner

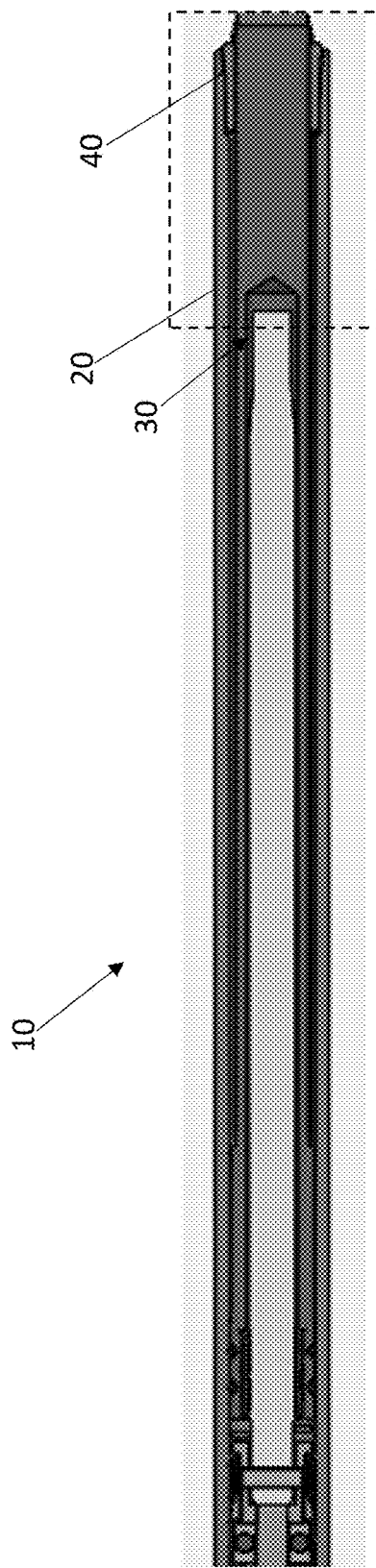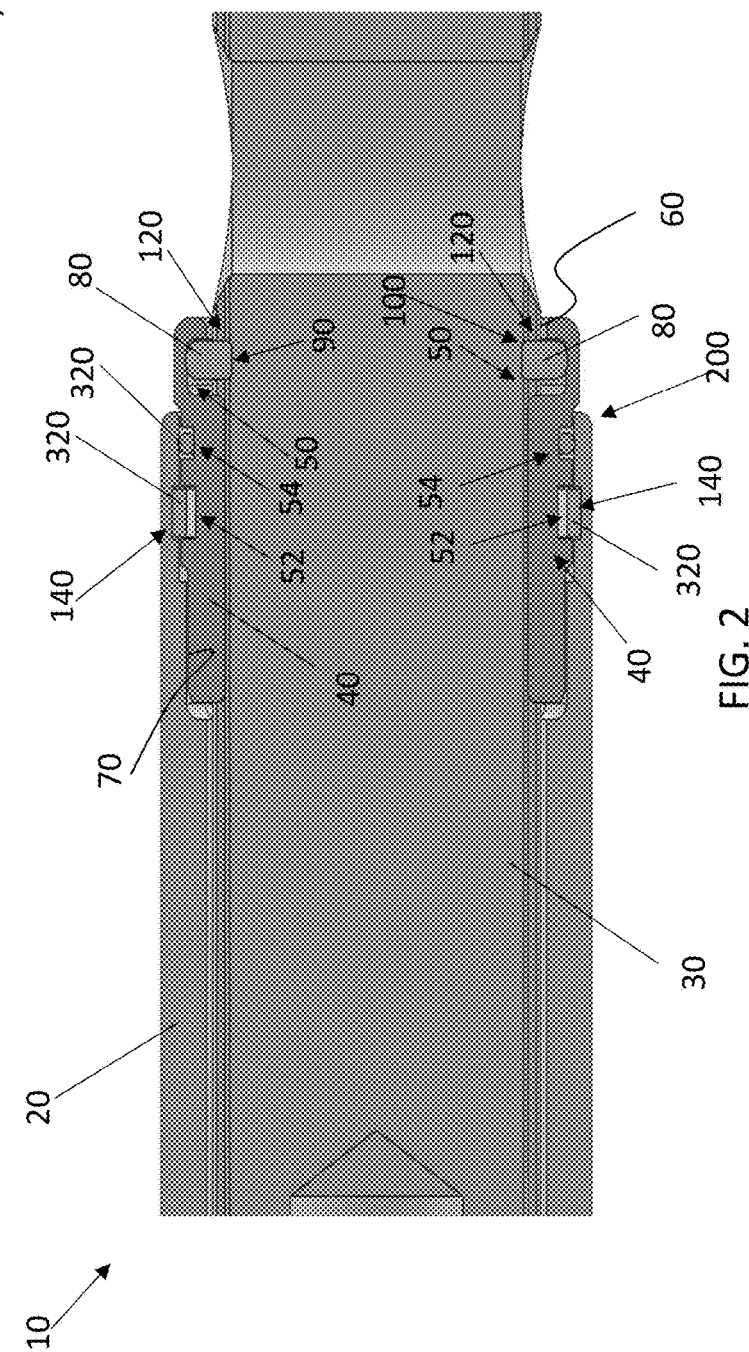

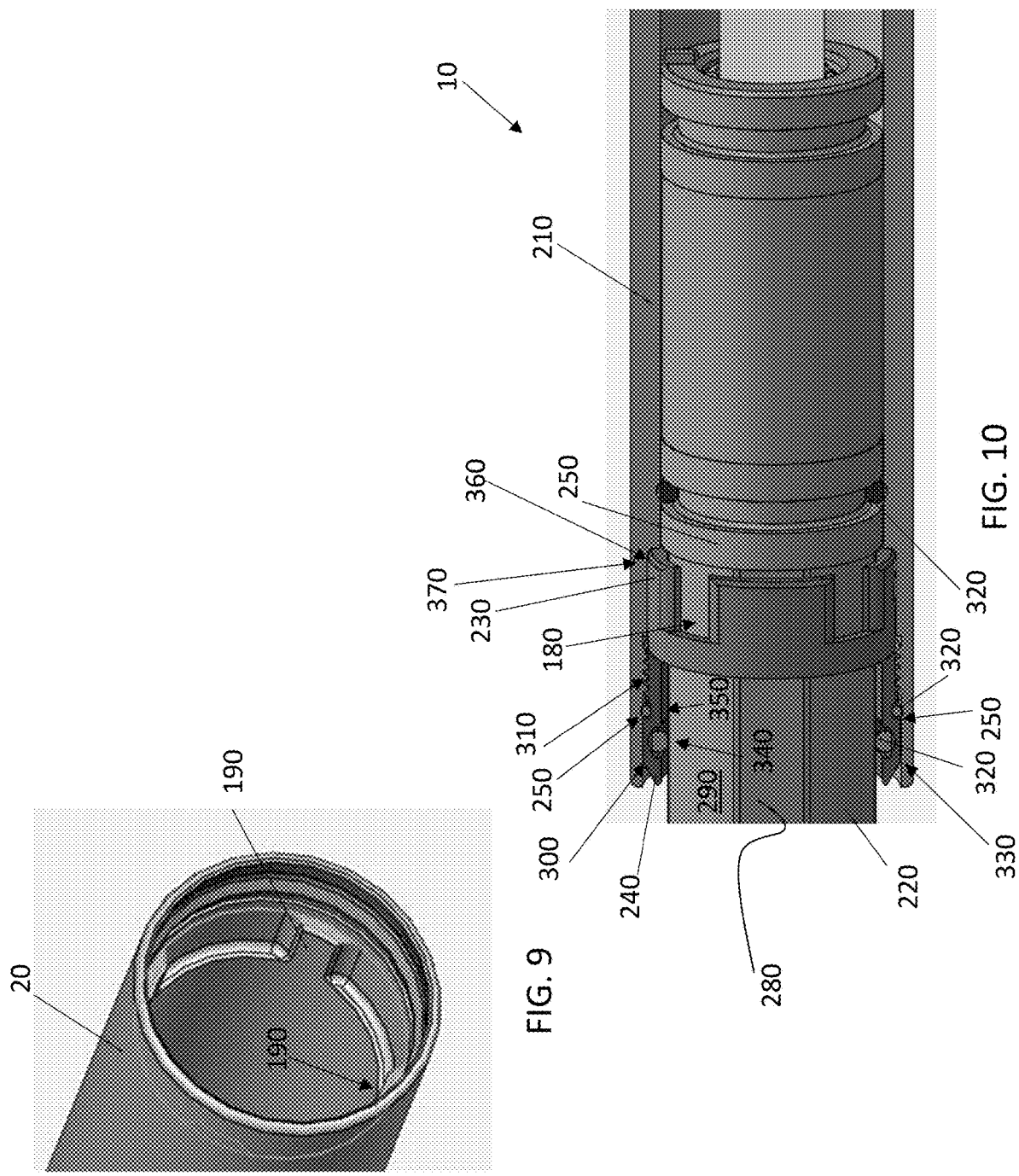

ADJUSTABLE IMPLANT WITH ADVANCED SEALING AND RETENTION

PRIORITY CLAIMS

This application claims priority to U.S. Provisional Application No. 63/197,192 (filed Jun. 4, 2021) and U.S. Provisional Application No. 63/209,987 (filed Jun. 12, 2021), each of which is incorporated by reference in its entirety.

TECHNICAL FIELD

The present disclosure relates to implantable devices. More particularly, the disclosure relates to an adjustable implant, such as a distraction and/or compression device, with advanced sealing and retention.

BACKGROUND

Generally, implanted medical devices are sealed against intrusion of bodily fluids after implantation. While intrusion resistance can be relatively easily for static implants, implants with moving parts can be challenging to seal.

SUMMARY

The needs above, as well as others, are addressed by embodiments of devices, and related methods described in this disclosure. All examples and features mentioned below can be combined in any technically possible way.

Various implementations include adjustable implants with sealing and/or retention features.

In particular aspects, an adjustable implant includes: a housing; an adjustable member at least partially positioned within the housing and configured to translate relative to the housing; and an intermediary member positioned between the housing and the adjustable member, the intermediary member including: a first groove facing an outer surface of the adjustable member; and a second groove facing an inner surface of the housing.

In additional particular aspects, an adjustable implant includes: a housing; an adjustable member at least partially positioned within the housing and configured to translate relative to the housing, the adjustable member including at least one flat portion; and an intermediary member positioned between the housing and the adjustable member, the intermediary member including at least one flat portion configured to mate with or engage the at least one flat portion of the adjustable member.

In further particular aspects, an adjustable implant includes: a housing; an adjustable member at least partially positioned within the housing and configured to translate relative to the housing; an intermediary member positioned between the housing and the adjustable member; and an endcap positioned proximate to the intermediary member and between the housing and the adjustable member.

In additional particular aspects, an adjustable implant includes: a housing having at least one flat portion; an adjustable member at least partially positioned within the housing and configured to translate relative to the housing, wherein the adjustable member includes at least one flat portion configured to mate with the at least one flat portion of the housing; an endcap disposed within the housing at an end of the housing interfacing with the adjustable member.

Implementations may include one of the following features, or any combination thereof.

In certain cases, the first groove is configured to receive an o-ring, a radial seal or a retainer therein.

In particular aspects, the second groove is configured to receive an o-ring, a radial seal or a retainer therein.

In some implementations, the first groove includes a substantially circular radial seal positioned therein, the radial seal including a first tab positioned on an opposing side of the radial seal from a second tab.

In certain aspects, the adjustable member includes a first cut-out and a second cut-out each positioned about the outer surface of the adjustable member, the first cut-out configured to receive the first tab of the radial seal therein and the second cut-out configured to receive the second tab of the radial seal therein.

In some cases, the housing includes a third groove extending about the inner surface of the housing, the third groove configured to complement the second groove facing the inner surface of the housing.

In particular implementations, the intermediary member includes at least one flat portion about an inner surface thereof.

In certain aspects, the adjustable member includes at least one flat portion about the outer surface thereof, the at least one flat portion of the adjustable member configured to mate with the at least one flat portion of the intermediary member.

In some cases, the at least one flat portion of the intermediary member includes four distinct flat portions and wherein the at least one flat portion of the adjustable member includes four distinct flat portions.

In particular aspects, the at least one flat portion of the intermediary member includes two distinct flat portions and wherein the at least one flat portion of the adjustable member includes two distinct flat portions.

In certain cases, interaction between the at least one flat portion on the outer surface of the adjustable member and the at least one flat portion of the intermediary member resists intrusion of fluid to a space between the adjustable member and the housing.

In particular implementations, interaction between the at least one flat portion on the outer surface of the adjustable member and the at least one flat portion of the intermediary member controls rotation of the adjustable member relative to the housing and provides both a static and dynamic seal for ingress protection.

In some aspects, the intermediary member is a lug.

In certain cases, the intermediary member substantially surrounds the adjustable member.

In particular aspects, the housing substantially surrounds the intermediary member.

In some aspects, the intermediary member is an endcap of the housing.

In certain implementations, an end of the housing is crimped or pressed to retain at least one of the intermediary member or an additional seal.

In particular cases, an end of the housing includes an extension extending from an end of the housing inward toward the adjustable member, the extension retaining at least one of the intermediary member or an additional seal.

In some implementations, the adjustable member includes a stop thereabout, and the intermediary member is disposed between the stop and the endcap.

In certain aspects, the intermediary member abuts the stop and the endcap.

In some cases, the endcap is configured to engage with an inner surface of the housing via threads.

In particular aspects, the endcap includes one or more grooves for housing a seal therein.

In certain implementations, the endcap includes a groove on an outer surface thereof for receiving a seal therein.

In some cases, the endcap includes a groove on an inner surface thereof for receiving a seal therein.

In particular aspects, the adjustable implant further includes a seal positioned between the adjustable member and the housing.

In some implementations, one of the housing and the intermediary member includes a first mating feature configured to mate with a second mating feature on the other one of the housing and the intermediary member.

Two or more features described in this disclosure, including those described in this summary section, may be combined to form implementations not specifically described herein.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

The details of one or more implementations are set forth in the accompanying drawings and the description below. Other features, objects and benefits will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings, FIG. 1 shows a cross sectional view of an adjustable implant according to embodiments of the disclosure;

FIG. 2 shows an enlarged cross-sectional view taken at box A of FIG. 1 according to one embodiment of the disclosure;

FIG. 9 shows a perspective view of the housing according to one embodiment of the disclosure;

FIG. 10 shows a cross-sectional perspective view of the adjustable implant according to one embodiment of the disclosure.

Figure 3:
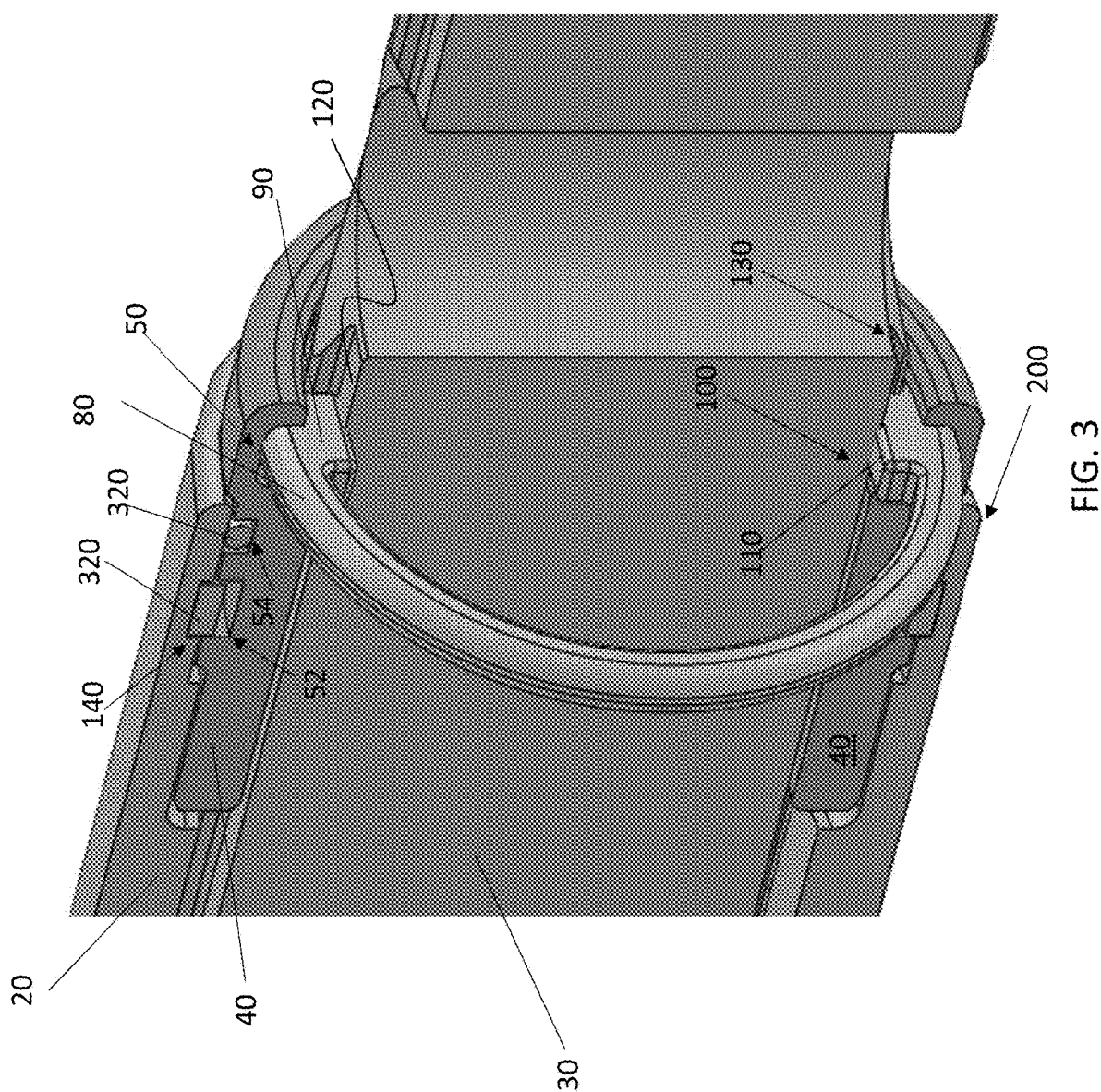
FIG. 3 shows a perspective cross-sectional view of FIG. 2 showing additional details of the radial seal.

It is noted that the drawings of the subject matter are not necessarily to scale. The drawings are intended to depict only typical aspects of the subject matter, and therefore, should not be considered as limiting the scope of the disclosed subject matter. In the drawings, like numbering represents like elements between the drawings.

DETAILED DESCRIPTION

Implanted medical devices can be sealed against intrusion of bodily fluids after implantation. This sealing can be important in objects with cavities containing electronics or other delicate components (e.g., implanted stimulators like pacemakers or neurostimulators). Effective sealing of implants can be challenging for expandable implants (e.g., telescoping expandable devices). Various conventional implanted lengthening devices use an interaction between a male tab and a female slot, which can be difficult to seal.

In contrast, various disclosed implementations beneficially employ one or more flat portions at device interfaces for resisting intrusion of fluid, and/or for anti-rotation purposes. These interfaces can include flat portions that aid with both static and dynamic sealing against fluid intrusion (i.e., ingress protection).

The present disclosure relates to an adjustable implant such as a distraction/compression device (e.g., a limb lengthening device, adjustable spinal rod, etc.). Disclosed examples can be used with any of a variety of devices, such as those described in U.S. Pat. No. 8,449,543 (filed Sep. 3, 2010); U.S. Pat. No. 8,974,463 (filed May 22, 2012); U.S. Pat. No. 9,044,281 (filed Oct. 18, 2012); and U.S. Pat. No. 10,271,885 (filed Dec. 28, 2015), the entireties of each of which are incorporated herein by reference for any and all purposes.

As shown in FIGS. 1-5 and 8, the adjustable implant 10 includes a housing 20; an adjustable member 30 at least partially positioned within the housing 20 and configured to translate relative to the housing 20; and an intermediary member 40 positioned between the housing 20 and the adjustable member 30. The intermediary member 40 can include a first groove 50 facing an outer surface 60 of the adjustable member 30 and a second groove 52 facing an inner surface 70 of the housing 20. In certain examples, the intermediary member 40 can further include an additional groove 54 facing the inner surface 70 of the housing 20. The intermediary member 40 can substantially surround the adjustable member 30. The housing 20 can substantially surround the intermediary member 40. In some embodiments, the intermediary member 40 is composed of a biocompatible metal (e.g., BIODUR).

The housing 20 is configured to couple with and/or affix to a first bone portion (not shown) and the adjustable member 30 is configured to couple with and/or affix to a second bone portion (not shown). Movement of the adjustable member 30 relative to the housing 20, and therefore, the second bone portion relative to the first bone portion, can result in osteogenesis between bone portions where the adjustable implant 10 is a limb lengthening device. Where the adjustable implant 10 is an adjustable spinal rod, movement of the adjustable member 30 relative to housing 20 can result in modifying a spinal curvature.

The grooves 50, 52, 54 of the intermediary member 40 are each configured to receive an o-ring, a radial seal or a retainer (e.g., seal member or retainer indicated by 320) therein. In one embodiment (see FIGS. 2-3), the first groove 50 includes a substantially circular radial seal 80 positioned therein. In one embodiment, the radial seal 80 includes a first tab 90 positioned on an opposing side 100 of the radial seal 80 from a second tab 110. In this embodiment, the adjustable member 30 includes a first cut-out 120 and a second cut-out 130 each positioned about the outer surface 60 of the adjustable member 30. The first cut-out 120 is configured to receive, mate with, and/or engage the first tab 90 of the radial seal therein and the second cut-out 130 is configured to receive the second tab 110 of the radial seal therein. In another embodiment, the reverse configuration is contemplated (e.g., one where the adjustable member 30 includes two opposing tabs and the radial seal 80 includes two opposing cut-outs configured to receive, mate with and/or engage two opposing tabs of the adjustable member 30).

Figure 6:
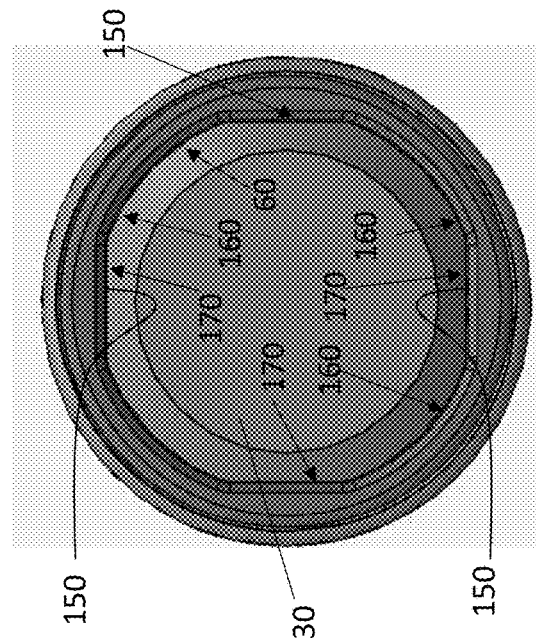
FIG. 6 shows a cross-sectional view of the adjustable implant taken along line B according to one embodiment of the disclosure.
Figure 7:
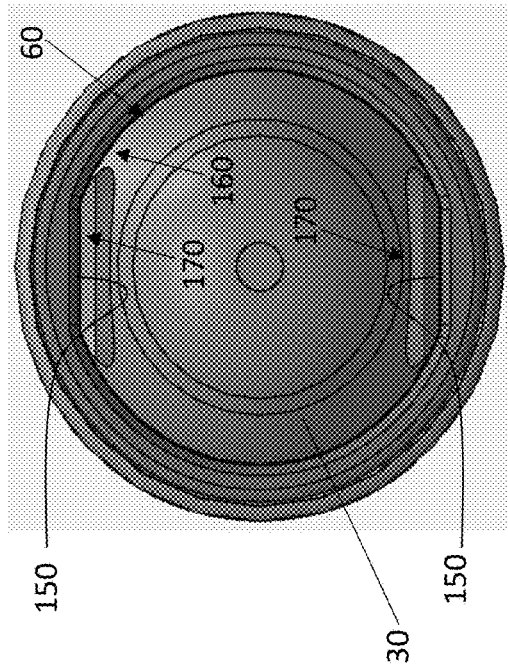
FIG. 7 shows a cross-sectional view of the adjustable implant taken along line B according to another embodiment of the disclosure.
Figure 5:
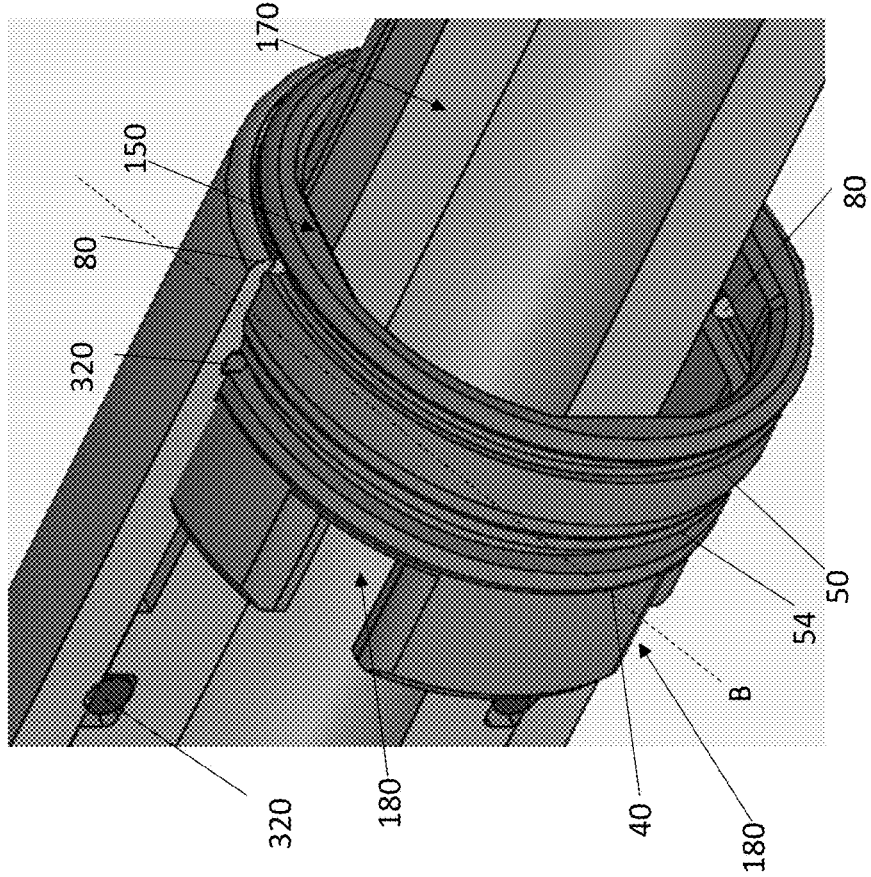
FIG. 5 shows a cross-sectional view of FIG. 4 shows additional details of the intermediary member.
Figure 8:
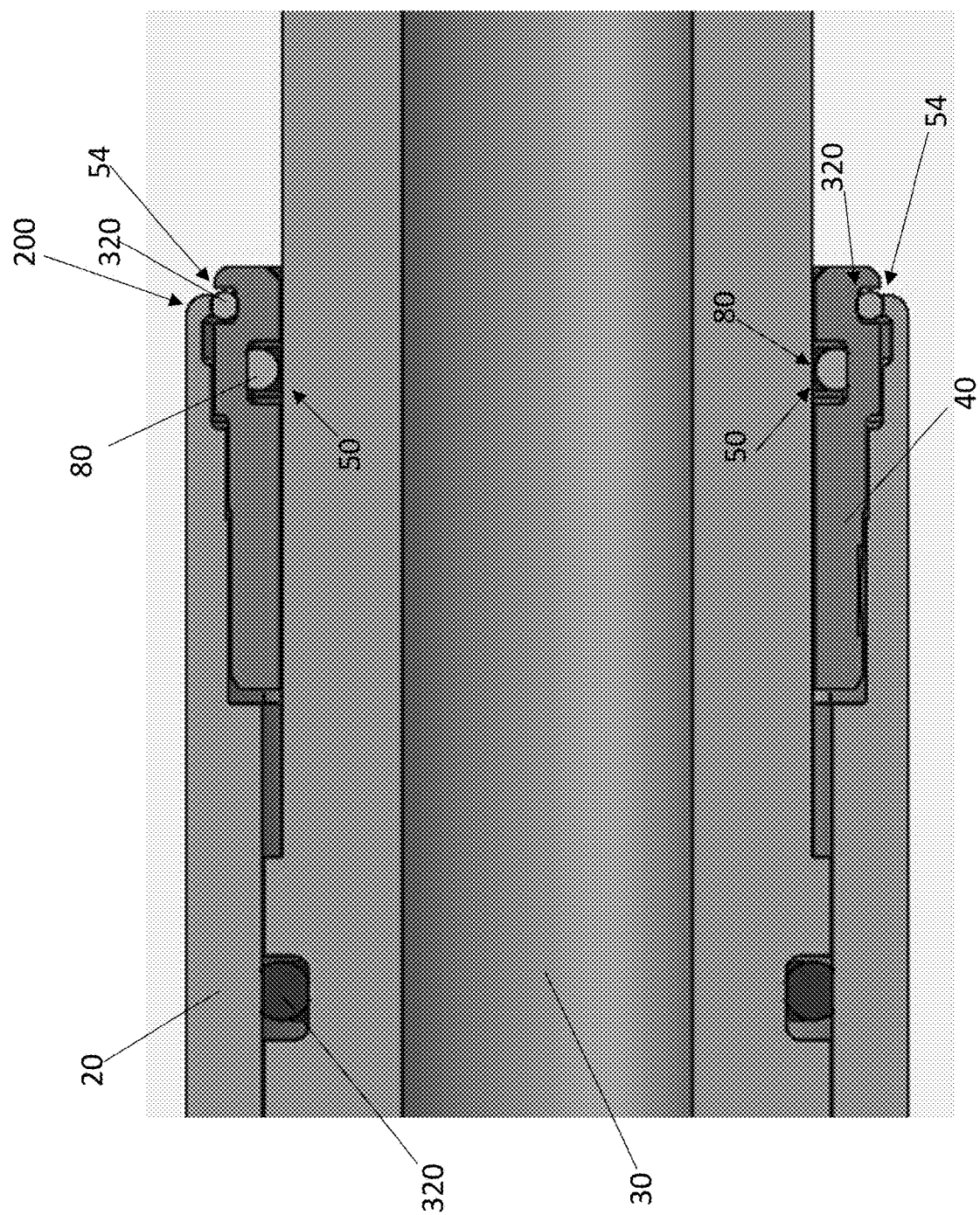
FIG. 8 shows a cross-sectional view taken at box A of FIG. 1 according to another embodiment of the disclosure.

In one embodiment, the housing 20 can include a groove (or, third groove) 140 extending about the inner surface 70 of the housing 20. The housing groove 140 is configured to complement the second groove 52 facing the inner surface 70 of the housing 20. In one embodiment, shown in FIGS. 5-7, the intermediary member 40 includes at least one flat portion 150 about an inner surface 160 thereof. In this embodiment, the adjustable member 30 also includes at least one flat portion 170 about the outer surface 60 thereof. The at least one flat portion 170 of the adjustable member 30 is configured to mate with and/or engage the at least one flat portion 150 of the intermediary member 40. The intermediary member 40 and the adjustable member 30 can include any number (e.g., 1, 2, 3, 4, 5, 6, 7, 8, etc.) of flat portions 150, 170, respectively, without departing from aspects of the disclosure. For example, in one embodiment, the intermediary member 40 and adjustable member 30 each include four flat portions 150, 170, respectively, as shown in FIG. 6, and in another embodiment, the intermediary member 40 and adjustable member 30 each include two flat portions 150, 170, as shown in FIG. 7.

In one embodiment, the intermediary member 40 is a lug. In another embodiment, the intermediary member 40 is an endcap of the housing 20. In one embodiment (see FIG. 5), the intermediary member 40 includes cut-outs 180 that receive, mate with and/or engage corresponding tabs 190 positioned within the housing 20 (see FIG. 9). Alternatively, the reverse configuration is contemplated such that the intermediary member 40 includes tabs and the housing includes corresponding cut-outs. These configurations can provide an anti-rotation feature or function.

In one embodiment, an end 200 (e.g., axial end) of the housing 20 is crimped or pressed to retain the intermediary member 40 and/or any seals (e.g., seals 320) which can be positioned proximate to the end of the housing 200. The crimped end portion 200 of the housing 20 can contact, engage with and/or mate with an angled end of the intermediary member 40. In another embodiment, an end 200 of the housing 20 includes an extension extending inward toward the adjustable member 30, the extension retaining the intermediary member 40 and/or any seals.

FIG. 10 shows another embodiment of the disclosure. In this embodiment, the adjustable implant 10 includes: a housing 210; an adjustable member 220 at least partially positioned within the housing 210 and configured to translate relative to the housing 210; an intermediary member 230 positioned between the housing 210 and the adjustable member 220; and an endcap 240 positioned proximate to the intermediary member 230 and between the housing 210 and the adjustable member 220. The adjustable member 220 can include a stop 250 thereabout. The intermediary member 230 is disposed between the stop 250 and the endcap 240. In some embodiments, the intermediary member 230 abuts the stop 250 and the endcap 240.

Further, the intermediary member 230 can include at least one flat portion on an inner surface thereof (obstructed in this view). The adjustable member 220 can include at least one flat portion 280 on an outer surface 290 thereof, where the at least one flat portion 280 of the adjustable member 220 is configured to mate with the at least one flat portion of the intermediary member 230. That is, each flat portion 280 on the outer surface 290 of the adjustable member 220 is configured to mate with a flat portion of the intermediary member 230.

The endcap 240 is configured to engage with an inner surface 300 of the housing 210 via threads 310. In some embodiments, the endcap 240 includes one or more grooves 250 for housing an o-ring, a radial seal or a retainer (shown as an example seal 320, FIG. 10) therein. For example, the endcap 240 can include a groove 250 on an outer surface 330 thereof for receiving an o-ring, a radial seal or a retainer (e.g., seal 320) therein. In some embodiments, the endcap 240 includes a groove 340 on an inner surface 350 thereof for receiving an o-ring, a radial seal or a retainer (e.g., a seal 320) therein. In additional implementations, a seal 320 (e.g., an o-ring, a radial seal or a retainer) may be positioned between the adjustable member 220 and the housing 210.

In some embodiments, one of the housing 210 and the intermediary member 230 can include a first mating feature 360 configured to mate with a second mating feature 370 on the other one of the housing 210 and the intermediary member 230. The mating features 360, 370 can include complementary mating features such as cutouts or female features, and tabs or male features.

Figure 11:
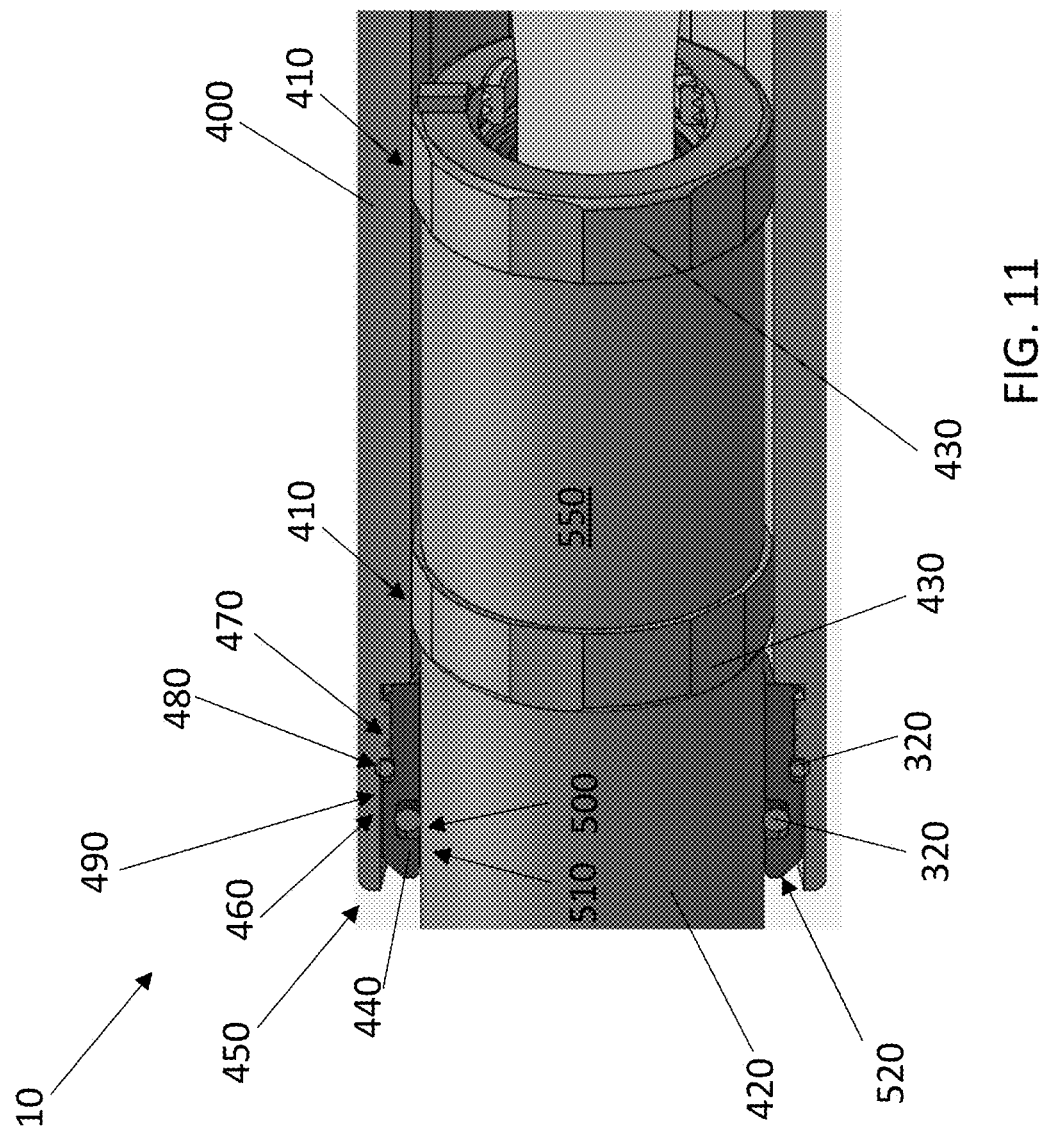
FIG. 11 shows a cross-sectional perspective view of the adjustable implant according to one embodiment of the disclosure.

FIG. 11 shows another embodiment of the disclosure. In this embodiment, the adjustable implant 10 includes a housing 400 having at least one flat portion 410, and an adjustable member 420 at least partially positioned within the housing 400 and configured to translate relative to the housing 400. In various implementations, the adjustable member 420 includes at least one flat portion 430 configured to mate with the at least one flat portion 410 of the housing 400. The adjustable implant 10 can further include an endcap 440 disposed within the housing 400 at an end 450 of the housing 400 interfacing with the adjustable member 420.

The endcap 440 is configured to engage with an inner surface 460 of the housing 400 via threads 470. In some embodiments, the endcap 440 includes one or more grooves 480 for housing an o-ring, a radial seal or a retainer (example seal(s) 320 shown in FIG. 11) therein. For example, the endcap 440 can include a groove 480 on an outer surface 490 thereof for receiving an o-ring, a radial seal or a retainer (e.g., seal 320) therein. In some embodiments, the endcap 440 includes a groove 500 on an inner surface 510 thereof for receiving an o-ring, a radial seal or a retainer (e.g., seal 480) therein. In certain additional implementations, a seal 480 (e.g., o-ring, a radial seal or a retainer) may be positioned between the adjustable member 420 and the housing 400. In some example implementations, the end 450 of the housing 400 is crimped or pressed to retain the endcap 440 and/or any seals which can be positioned proximate the end 450 of the housing 400. The crimped end portion 450 of the housing 400 can contact, engage with and/or mate with an angled end 520 of the endcap 440. In some cases, the adjustable member 420 can include one or more flat portions 410. For example, the adjustable member 420 can include one or more (e.g., axially arranged, and in some cases axially separated) rows of flat portions 430 positioned circumferentially about an outer surface 550 of the adjustable member 420. The housing 400 can include one or more flat portions 410 for mating with the one or more flat portions 430 of the adjustable member 420 in a manner analogous to the manner shown and described relative to FIGS. 6-7. For example, the housing 400 can include one or more rows of flat portions 410 positioned circumferentially about an inner surface of the housing, where the rows are axially arranged and in some cases axially separated. Interaction of the flat portions 410, 430 can provide an anti-rotation feature in various implementations.

Figure 4:
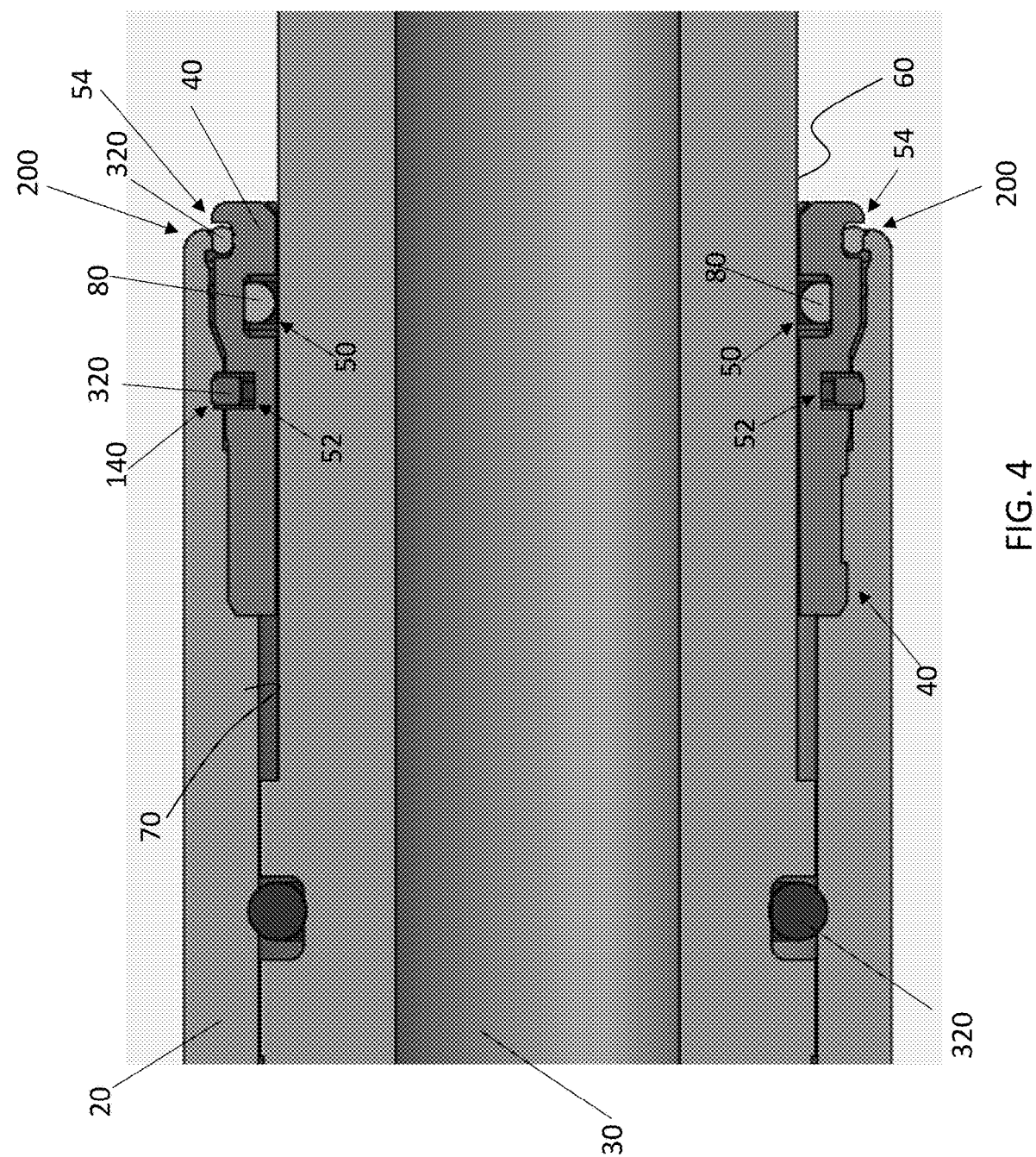
FIG. 4 shows a cross-sectional view taken at box A of FIG. 1 according to another embodiment of the disclosure.

In another embodiment, the endcap 440 of FIG. 11 could be retained within the housing 400 similar to the intermediary member of FIGS. 2 and 4, i.e., via an o-ring, a radial seal or a retainer, instead of with threads.

In certain example implementations, interfaces including flat portions of surfaces can enable resistance to fluid intrusion and/or rotation control. In certain of these cases, the interfaces formed by the flat portions, e.g., flat portions 150, 170; 280; and 410, 430, can provide both static and dynamic sealing for ingress protection, e.g., to avoid ingress of fluid into the adjustable implants shown and described herein. The disclosed implementations can have particular benefits for adjustable implants, that is, implants configured to distract and/or compress portions of a patient's bone. That is, the adjustable implants shown and described with respect to various implementations can beneficially enable bone distraction and/or compression (with movable parts) while also providing desirable ingress protection. In particular examples, the adjustable implants are configured to provide static and dynamic sealing of the adjustable member from external fluids, e.g., while the adjustable member translates relative to the housing.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

Commonly labeled components in the FIGURES are considered to be substantially equivalent components for the purposes of illustration, and redundant discussion of those components is omitted for clarity.

In various implementations, components described as being "coupled" to one another can be joined along one or more interfaces. In some implementations, these interfaces can include junctions between distinct components, and in other cases, these interfaces can include a solidly and/or integrally formed interconnection. That is, in some cases, components that are "coupled" to one another can be simultaneously formed to define a single continuous member. However, in other implementations, these coupled components can be formed as separate members and be subsequently joined through known processes (e.g., soldering, fastening, ultrasonic welding, bonding). In various implementations, electronic components described as being "coupled" can be linked via conventional hard-wired and/or wireless means such that these electronic components can communicate data with one another. Additionally, sub-components within a given component can be considered to be linked via conventional pathways, which may not necessarily be illustrated.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The terminology used herein is for the purpose of describing particular embodiments only and is not intended to be limiting of the disclosure. As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. It will be further understood that the terms "comprises" and/or comprising," when used in this specification, specify the presence of stated features, integers, steps, operations, elements, and/or components, but do not preclude the presence or addition of one or more other features, integers, steps, operations, elements, components, and/or groups.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

We claim:

1. An adjustable implant comprising:
a housing;
an adjustable member at least partially positioned within the housing and configured to translate relative to the housing, the adjustable member including a set of cut-outs positioned about an outer surface thereof; and
an intermediary member positioned between the housing and the adjustable member, the intermediary member including:
a first groove facing the outer surface of the adjustable member, wherein the first groove includes a substantially circular radial seal positioned therein, the radial seal including a first tab positioned on an opposing side of the radial seal from a second tab, wherein the first tab is engaged with a first cut-out in the set of cut-outs and the second tab is engaged with a second cut-out in the set of cut-outs,
wherein the first cut-out includes a flat surface that interfaces with a flat surface of the first tab, and wherein the second cut-out includes a flat surface that interfaces with a flat surface of the second tab; and
a second groove facing an inner surface of the housing, wherein the second groove is configured to receive an o-ring, a radial seal or a retainer therein, and wherein an axial end of the housing is crimped to retain the intermediary member and the o-ring, radial seal or retainer in the second groove.

2. The adjustable implant of claim 1, wherein the first tab and the second tab each include a protrusion extending radially inward from a body of the radial seal.

3. The adjustable implant of claim 1, wherein the housing includes a third groove extending about the inner surface of the housing, the third groove configured to complement the second groove facing the inner surface of the housing.

4. The adjustable implant of claim 1, wherein the intermediary member is a lug, or an endcap of the housing.

5. The adjustable implant of claim 1, wherein the intermediary member substantially surrounds the adjustable member.

6. The adjustable implant of claim 1, wherein the housing substantially surrounds the intermediary member.

7. The adjustable implant of claim 1, wherein the interface between the first tab and the first cut-out and the interface between the second tab and the second cut-out maintains a position of the axial seal relative to the adjustable member.

8. The adjustable implant of claim 1, further comprising:
a third groove on an inner surface of the housing and aligned with the second groove on the intermediate member; and
a seal member or retainer in the third groove.

9. An adjustable implant comprising:
a housing;
an adjustable member at least partially positioned within the housing and configured to translate relative to the housing, wherein the adjustable member includes at least one flat portion about an outer surface thereof, wherein the at least one flat portion is located between a plurality of arcuate sections of the outer surface; and
an intermediary member positioned between the housing and the adjustable member, the intermediary member including:
a first groove facing the outer surface of the adjustable member; and
a second groove facing an inner surface of the housing, wherein the second groove is configured to receive an o-ring, a radial seal or a retainer therein, and wherein an axial end of the housing is crimped to retain the intermediary member and the o-ring, radial seal or retainer in the second groove
wherein the intermediary member includes at least one flat portion about an inner surface thereof, and wherein the at least one flat portion of the adjustable member is configured to mate with the at least one flat portion of the intermediary member.

10. The adjustable implant of claim 9, wherein the at least one flat portion of the intermediary member includes four distinct flat portions and wherein the at least one flat portion of the adjustable member includes four distinct flat portions separated by the plurality of arcuate sections along the outer surface of the adjustable member.

11. The adjustable implant of claim 9, wherein the at least one flat portion of the intermediary member includes two distinct flat portions and wherein the at least one flat portion of the adjustable member includes two distinct flat portions separated by the plurality of arcuate sections along the outer surface of the adjustable member.

12. The adjustable implant of claim 9, wherein interaction between the at least one flat portion on the outer surface of the adjustable member and the at least one flat portion of the intermediary member resists intrusion of fluid to a space between the adjustable member and the housing.

13. The adjustable implant of claim 9, wherein interaction between the at least one flat portion on the outer surface of the adjustable member and the at least one flat portion of the intermediary member controls rotation of the adjustable member relative to the housing and provides both a static and dynamic seal for ingress protection.

14. The adjustable implant of claim 9, wherein the intermediary member is a lug, or an endcap of the housing.

15. The adjustable implant of claim 9, wherein the intermediary member substantially surrounds the adjustable member.

16. The adjustable implant of claim 9, wherein the housing substantially surrounds the intermediary member.

17. The adjustable implant of claim 9, further comprising a substantially circular radial seal positioned in the first groove.

* * * * *